(12) United States Patent
Lange et al.

(10) Patent No.: US 7,306,656 B2
(45) Date of Patent: Dec. 11, 2007

(54) GAS CHROMATOGRAPHY APPARATUS

(75) Inventors: Lutz Lange, Mainz (DE); Frank Helleis, Mainz (DE); Jonathan Williams, Mainz (DE); Thomas Kenntner, Mainz (DE)

(73) Assignee: Max-Planck-Gesellschaft zur Forderung der Wissenschaften e.V., Munich (DE)

( * ) Notice: Subject to any disclaimer, the term of this patent is extended or adjusted under 35 U.S.C. 154(b) by 171 days.

(21) Appl. No.: 11/356,965

(22) Filed: Feb. 17, 2006

(65) Prior Publication Data
US 2006/0191414 A1 Aug. 31, 2006

(30) Foreign Application Priority Data
Feb. 25, 2005 (EP) ................. 05004152

(51) Int. Cl.
*B01D 53/02* (2006.01)
(52) U.S. Cl. ................. 96/101; 96/105; 95/87
(58) Field of Classification Search ................. 96/101, 96/104, 105, 106; 95/82, 85, 87; 73/23.35, 73/23.39, 23.41, 23.42
See application file for complete search history.

(56) References Cited

U.S. PATENT DOCUMENTS

| 3,305,000 | A | * | 2/1967 | Bullen et al. ................. 165/260 |
| 4,732,581 | A | * | 3/1988 | Cheh et al. ................. 95/87 |
| 5,152,176 | A | * | 10/1992 | Bryselbout et al. ........ 73/23.41 |
| 5,588,988 | A | * | 12/1996 | Gerstel et al. ................ 96/101 |
| 5,596,876 | A | * | 1/1997 | Manura et al. .............. 62/55.5 |
| 5,778,681 | A | | 7/1998 | Li et al. |
| 5,807,426 | A | * | 9/1998 | Ohtsuki et al. ............... 96/102 |
| 6,165,251 | A | * | 12/2000 | Lemieux et al. ............... 95/82 |
| 6,190,613 | B1 | * | 2/2001 | Watanabe et al. ............. 422/99 |
| 6,385,973 | B1 | | 5/2002 | Moran |
| 6,514,316 | B1 | * | 2/2003 | Gaisford et al. ............... 95/87 |
| 6,547,852 | B2 | * | 4/2003 | Ledford et al. ................ 95/87 |
| 6,907,796 | B2 | * | 6/2005 | Bremer et al. ........... 73/863.11 |
| 2002/0134088 | A1 | | 9/2002 | Rudick et al. |

FOREIGN PATENT DOCUMENTS

| EP | 0 488 942 A2 | 6/1992 |
| EP | 1 312 875 A1 | 5/2003 |

* cited by examiner

*Primary Examiner*—Duane Smith
*Assistant Examiner*—Robert A Clemente
(74) *Attorney, Agent, or Firm*—Caesar, Rivise, Bernstein, Cohen & Pokotilow, Ltd.

(57) ABSTRACT

The invention relates to a gas chromatography apparatus with a cooling device, wherein the cooling device includes a closed cooling circuit containing a refrigerant, so that no refrigerant is wasted.

15 Claims, 4 Drawing Sheets

US 7,306,656 B2

GAS CHROMATOGRAPHY APPARATUS

BACKGROUND

The invention relates to a gas chromatography apparatus.

Gas chromatography apparatuses (GCs) are well-known in the state of the art. These well-known gas chromatography apparatuses comprise a coiled separation column for separating sample components. The separation column is installed in a heatable oven and has a downstream connection with a detector, which detects the different sample components. Further, the separation column comprises an upstream connection with an adsorbent, which is installed in a cold trap. During operation of this type of gas chromatography apparatuses there are two different phases of operation, which will be described in the following.

In the first phase of operation the adsorbent is loaded with the sample components, e.g., atmospheric air containing pollutants. The atmospheric air containing the pollutants is pumped or drawn through the adsorbent, which is cooled during the loading phase. Therefore, the pollution substances contained in the atmospheric air are concentrated in the adsorbent.

After this loading phase, the cooling of the adsorbent is stopped and both the adsorbent and the separation column are heated. Then, the pollution substances concentrated in the adsorbent are purged out of the adsorbent and swept by a gas through the separation column so that the detector detects the different separated pollution substances.

In common gas chromatography apparatus according to the state of the art, the cooling of the cold trap containing the adsorbent is effected by injecting a refrigerant (e.g., liquid nitrogen) into the cold trap, where the liquid nitrogen vaporizes thereby cooling the adsorbent. However, this type of cooling results in a high consumption of the refrigerant.

Therefore, it is an object of the invention to reduce the consumption of the refrigerant in such a gas chromatography apparatus.

SUMMARY OF THE INVENTION

The invention includes the use of a novel cooling device, which comprises a closed cooling circuit containing the refrigerant. Due to the closeness of the cooling circuit of the gas chromatography apparatus of the invention, effectively no refrigerant is wasted, so that the operation of the gas chromatography apparatus is much cheaper than the apparatus of the common gas chromatography apparatuses.

In a preferred embodiment of the invention the cooling circuit cools both the cold trap containing the adsorbent (e.g., a coiled column) and the oven containing the separation column. However, it is alternatively possible that the cooling circuit cools the cold trap only, whereas the oven is not cooled by the cooling device.

As with devices, the gas chromatography apparatus of the invention preferably comprises an oven with a heating device and a separation column for separating sample components, wherein the separation column is located within the oven.

Further, the gas chromatography apparatus according to the invention preferably comprises a cold trap containing the adsorbent (e.g., a coiled column), wherein the adsorbent has a downstream connection with the separation column.

In a preferred embodiment of the invention, the cooling circuit comprises a first branch for cooling the oven and a second branch for cooling the cold trap, so that the oven and the cold trap can be cooled by different branches of the same cooling circuit.

However, it is alternatively possible that separate cooling circuits are provided for the oven and for the cold trap.

Further, the heating device for heating the oven and/or the adsorbent preferably comprises a first heater for heating the oven and a second heater for heating the cold trap, so that the oven and the cold trap can be heated independently from each other.

In the preferred embodiment the cooling device comprises a compressor for compressing the refrigerant and for pumping the refrigerant through the cooling circuit. Further, the cooling device preferably comprises an evaporator for evaporating the compressed refrigerant thereby dissipating evaporation heat. Moreover, the cooling device preferably comprises a condenser for condensing the refrigerant thereby generating evaporation heat, so that the refrigerant is heated.

Further, the evaporator is preferably included and/or integrated in the oven. For example, the oven itself can be the evaporator, so that it is not necessary to provide a separate evaporator. In such an embodiment the refrigerant is introduced directly into the oven, where the refrigerant vaporizes thereby cooling the oven. Then, the vaporized refrigerant is pumped out of the oven to close the cooling circuit. Therefore, the oven is preferably gas-proof and comprises an inlet for introducing the refrigerant into the oven and an outlet for draining the refrigerant out of the oven. In this embodiment, the volume of the oven constitutes a part of the closed cooling circuit. This embodiment has the advantage that it is not necessary to provide a separate evaporator so that the weight and the installation space of the gas chromatographic apparatus are significantly reduced. Particularly, it is possible that the gas chromatography apparatus according to the invention is portable.

Further, the cold trap containing the adsorbent and the oven containing the separation column are preferably thermally insulated from each other. This is particularly important in the aforementioned embodiment in which the cold trap and the oven can be cooled and/or heated independently from each other in order to obtain different temperatures in the cold trap and in the oven.

Further, the cooling device preferably actively cools the oven and/or the cold trap.

In a preferred embodiment the oven and/or the cold trap comprises thermal insulation at least partially comprising a foam. For example, the thermal insulation can be made of calcium silicate or Promasil®.

Further, there is preferably a rotary fan disposed within the oven for generating a stream thereby minimizing temperature gradients within the oven. The stream generated by the rotary fan minimizes temperature differences within the oven, which allows an accurate control of the temperature of the separation column.

In a preferred embodiment of the gas chromatography apparatus, there is a cylindrical guide plate disposed within the oven for guiding the stream generated by the rotary fan. The guide plate preferably surrounds the rotary fan coaxially so that the stream generated by the rotary fan is aligned coaxially within the cylindrical guide plate.

In this embodiment, there is preferably an annular gap between the cylindrical guide plate and the cylindrical inner wall of the oven, so that the inner stream generated by the rotary fan within the cylindrical guide plate is returned through the annular gap. In this embodiment, the coiled separation column is preferably disposed within the annular gap so that the return stream in the annular gap effectively controls the temperature of the separation column.

The rotary fan preferably comprises a rotation speed of at least 500 revolutions per minute. Therefore, the rotary fan can be driven by an electric motor, which is preferably housed outside the oven.

It was already mentioned above that the heating device for heating the oven and/or the cold trap preferably comprises an electrical heater, e.g., an electrical resistor. However, the invention is not restricted to this type of an electrical heater.

Further, it is understood that the gas chromatography apparatus of the invention can be connected to any type of detector at the outlet of the separation column. For example, a mass spectrometer, a flame ionization detector, a time-of-flight-mass-spectrometer or a pulse discharged detector can be used for detecting the different sample components, which are separated by the separation column.

Further, it is understood that both the separation column and the adsorbent can be in the form of a coiled capillary pipe. However, it is alternatively possible to use glass beads as a surface on which gas may be condensed.

The gas chromatography apparatus of the inventions facilitates reducing the temperature within the cold trap and/or within the oven down to at least 0° C., −5° C., −10° C., −20° C., −30° C. or −40° C.

Further, the heating device is preferably adapted to raise the temperature within the oven and/or within the cold trap up to at least +50° C., +100° C., +150° C., +200° C., +250° C. or +300° C.

Finally, it is understood that any type of common refrigerant can be used in the gas chromatograph according to the invention. For example, Freon can be used as a refrigerant.

BRIEF DESCRIPTION OF SEVERAL VIEWS OF THE DRAWINGS

In the following, a preferred embodiment of the invention is described referring to the drawings.

DETAILED DESCRIPTION OF PREFERRED EMBODIMENTS OF THE INVENTION

Figure 1:
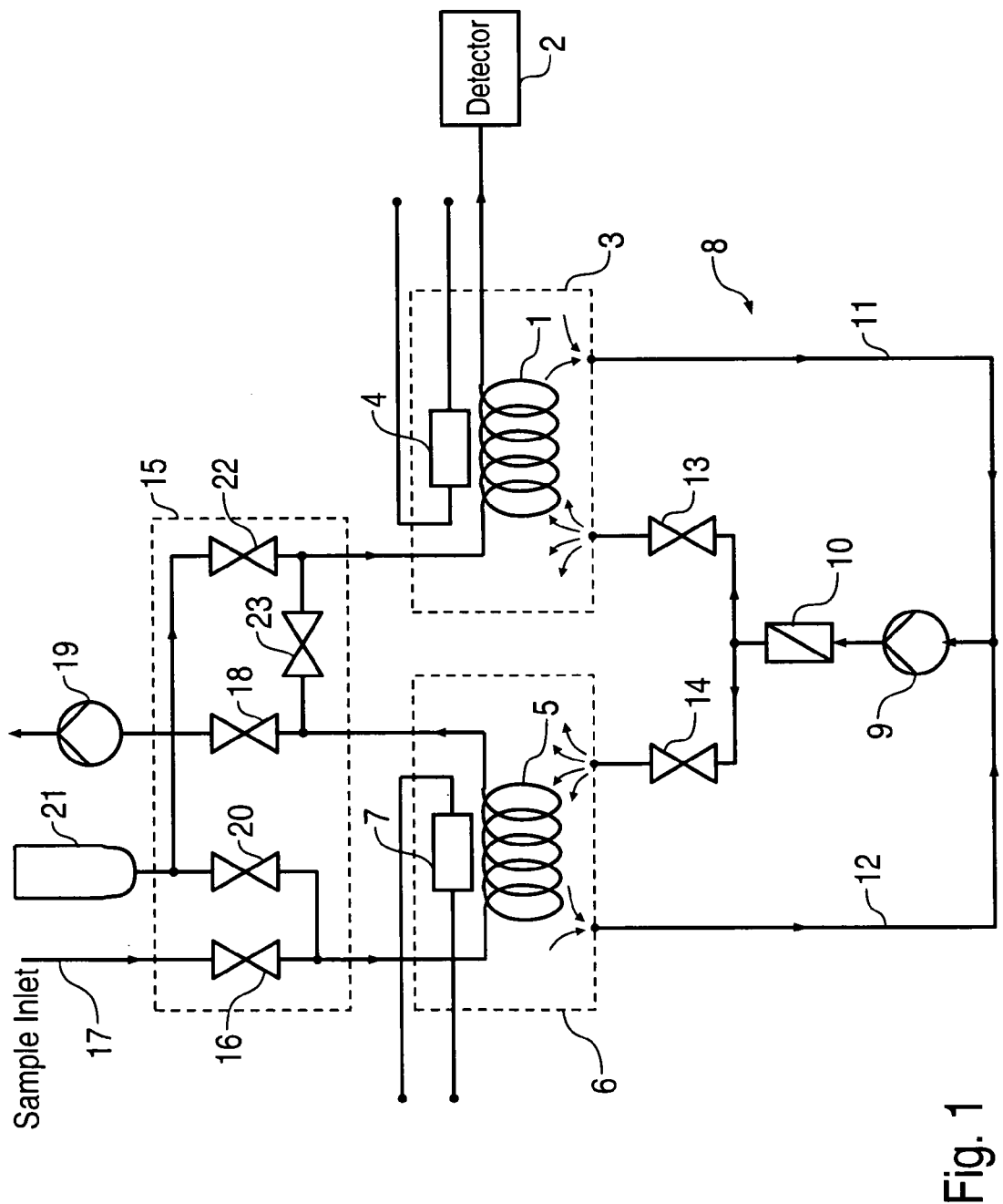
FIG. 1 shows a schematic diagram of a preferred embodiment of the gas chromatography apparatus according to the invention.

The gas chromatography apparatus according to the drawings comprises a coiled separation column 1 for separating sample components according to the well-known principles of gas chromatography.

The separation column 1 has a downstream connection with a detector 2, which detects the different constituents of the sample. In this particular embodiment the detector 2 is a mass-spectrometer. However, any other type of detector can be used instead of the detector 2.

The separation column 1 is disposed within a gas-proof oven 3 which can be heated by an electrical heater 4.

Further, the gas chromatography apparatus comprises an adsorbent 5, which is enclosed within a gas-tight cold trap 6 being heatable by another electrical heater 7, which is well-known from common gas chromatography apparatuses.

Therefore, the cold trap 6 with the adsorbent 5 and the oven 3 with the separation column 1 can be heated independently from each other. However, the operation of the electrical heaters 4, 7 will be described in detail later.

Further, the gas chromatography apparatus comprises a cooling circuit 8 for cooling the oven 3 and the cold trap 6.

The cooling circuit 8 comprises a compressor 9 for compressing and pumping a refrigerant through the closed cooling circuit 8.

Further, the cooling circuit 8 comprises a condenser 10 for cooling down the compressed refrigerant, which is common in such cooling devices.

Moreover, the cooling circuit 8 comprises a branch 11 for cooling the oven 3 and another branch 12 for cooling the cold trap 6.

Control valves 13, 14 are disposed in each of the branches 11, 12 of the cooling circuit 8, so that the oven 3 and the cold trap 6 can be cooled independently from each other.

In this embodiment, both the oven 3 and the cold trap 6 are gas-proof cylindrical chambers in which the refrigerant is introduced and from which the refrigerant is drained. Therefore, it is not necessary to provide a separate vaporizer as in common cooling devices known in the state of the art. The gas chromatography apparatus according to the invention therefore has a reduced weight and a reduced installation space. In fact, the gas chromatography apparatus according to the preferred embodiment is even portable.

Further, the gas chromatography apparatus according to the invention comprises a valve unit 15 controlling the flow through separate inlets and outlets of the gas chromatography apparatus.

Particularly, the valve unit 15 comprises an inlet valve 16 connecting the adsorbent 5 with an inlet 17 for suction of ambient air to be analysed. Further, the valve unit 15 comprises a pump outlet valve 18 connecting the outlet of the adsorbent 5 with a suction pump 19. Moreover, the inlet of the adsorbent 5 is connected by a purging valve 20 with a pressurized carrier gas tank 21. The carrier gas tank 21 is further connected by a purging valve 22 with the inlet of the separation column 1. Finally, the outlet of the adsorbent 5 is connected by a connection valve 23 with the inlet of the separation column 1.

Figure 2:
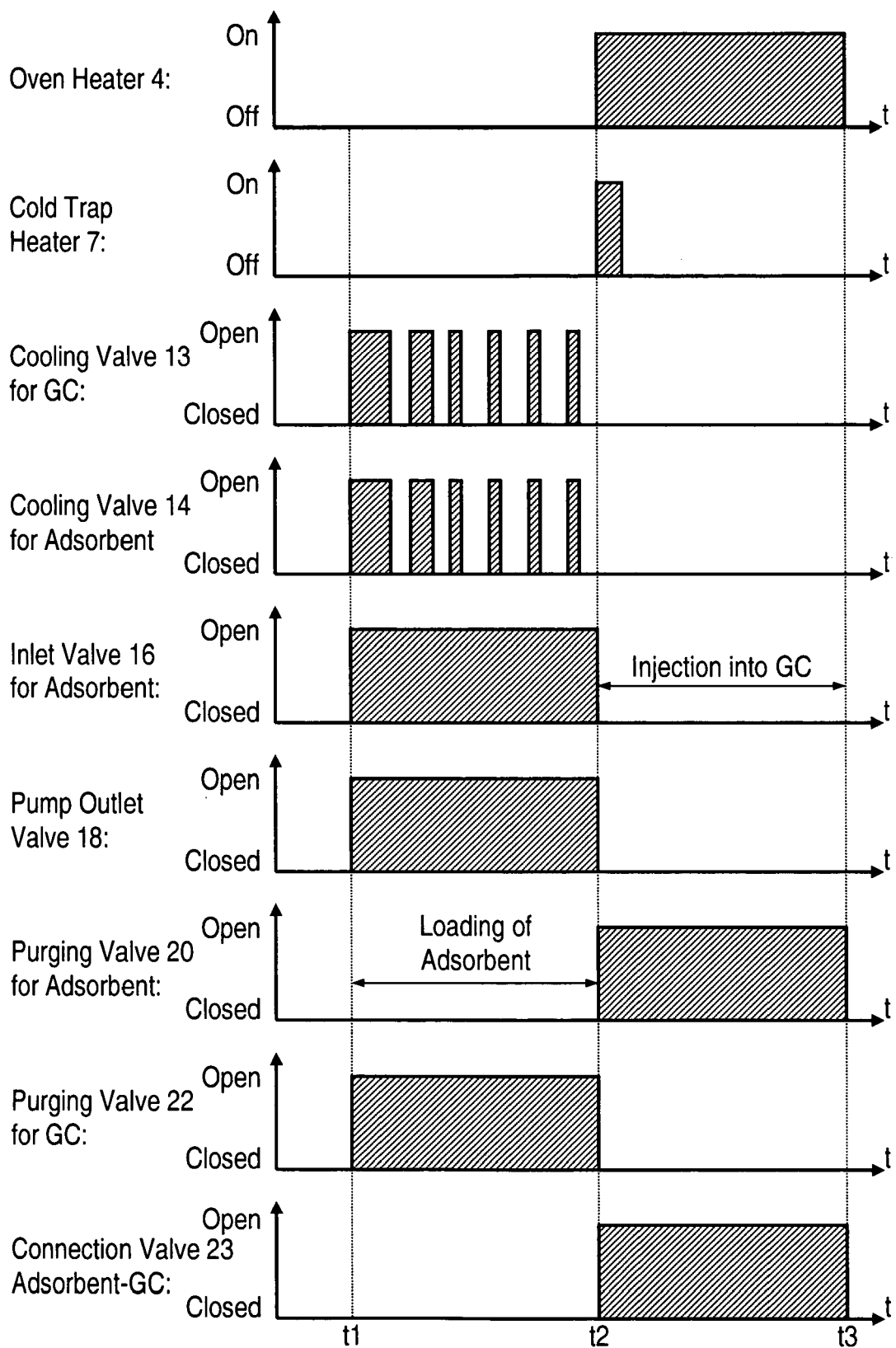
FIG. 2 shows a timing diagram of the operation of the gas chromatography apparatus according to FIG. 1.

In the following, the operation of the gas chromatography apparatus according to FIG. 1 is described referring to the timing diagram shown in FIG. 2.

The operation of the gas chromatography apparatus is divided into two phases following each other.

In the first phase between t=t1 and t=t2 the adsorbent 5 is loaded with sample substances contained in ambient air, which is sucked in by the suction pump 19 via the pump outlet valve 18, the inlet valve 16 and the inlet 17. Therefore, both the inlet valve 16 and the pump outlet valve 18 are opened during the loading of the adsorbent 5 between t=t1 and t=t2. Further, the purging valve 20 and the connection valve 23 are both closed. However, the purging valve 22 is opened, so that the separation column 1 is purged with carrier gas (e.g. helium) during the loading of the adsorbent 5.

During the loading of the adsorbent 5 between t=t1 and t=t2 the control valves 13, 14 of the cooling circuit 8 are temporarily opened and the compressor 9 is working, so that both the oven 3 and the cold trap 6 are being cooled. The cooling of the cold trap 6 during the loading of the adsorbent 5 is necessary in order to reach a concentration of the sample constituents (e.g. air pollution substances) within the adsorbent 5. The temperature in the cold trap 6 and in the oven 3 is controlled by a closed-loop controller, which adjusts the opening and closing times of the control valves 13, 14.

At the end of the loading phase at t=t2 the inlet valve 16, the pump outlet valve 18, the purging valve 22 and the control valves 13, 14 are closed. Therefore, the cooling circuit 8 stops the cooling of the oven 3 and the cold trap 6 at t=t2. Further, after t=t2 the purging of the separation columns 1 is stopped by closing the purging valve 22.

In the second phase of operation between t=t2 and t=t3 the sample constituents concentrated in the adsorbent 5 are injected into the separation column 1 for detection by the detector 2.

Therefore, the purging valve 20 and the connection valve 23 are opened, so that carrier gas from the carrier gas tank 21 flows through the adsorbent 5 and the separation column 1, where the sample constituents are separated from each other and finally detected by the detector 2.

Figure 3:
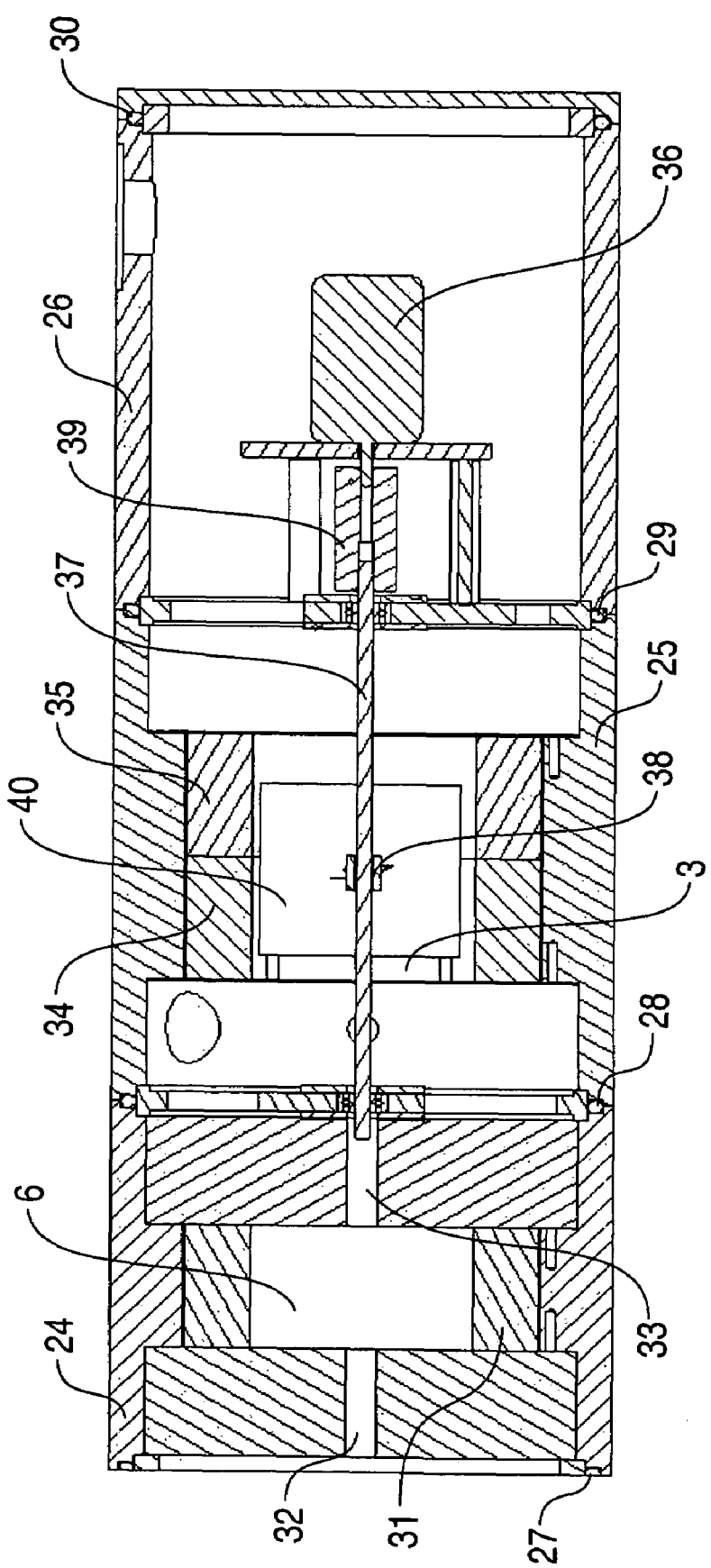
FIG. 3 shows a sectional view of the gas chromatography apparatus to claim 1 and FIG. 4 shows a perspective view of the gas chromatograph as shown in FIG. 3.
Figure 4:
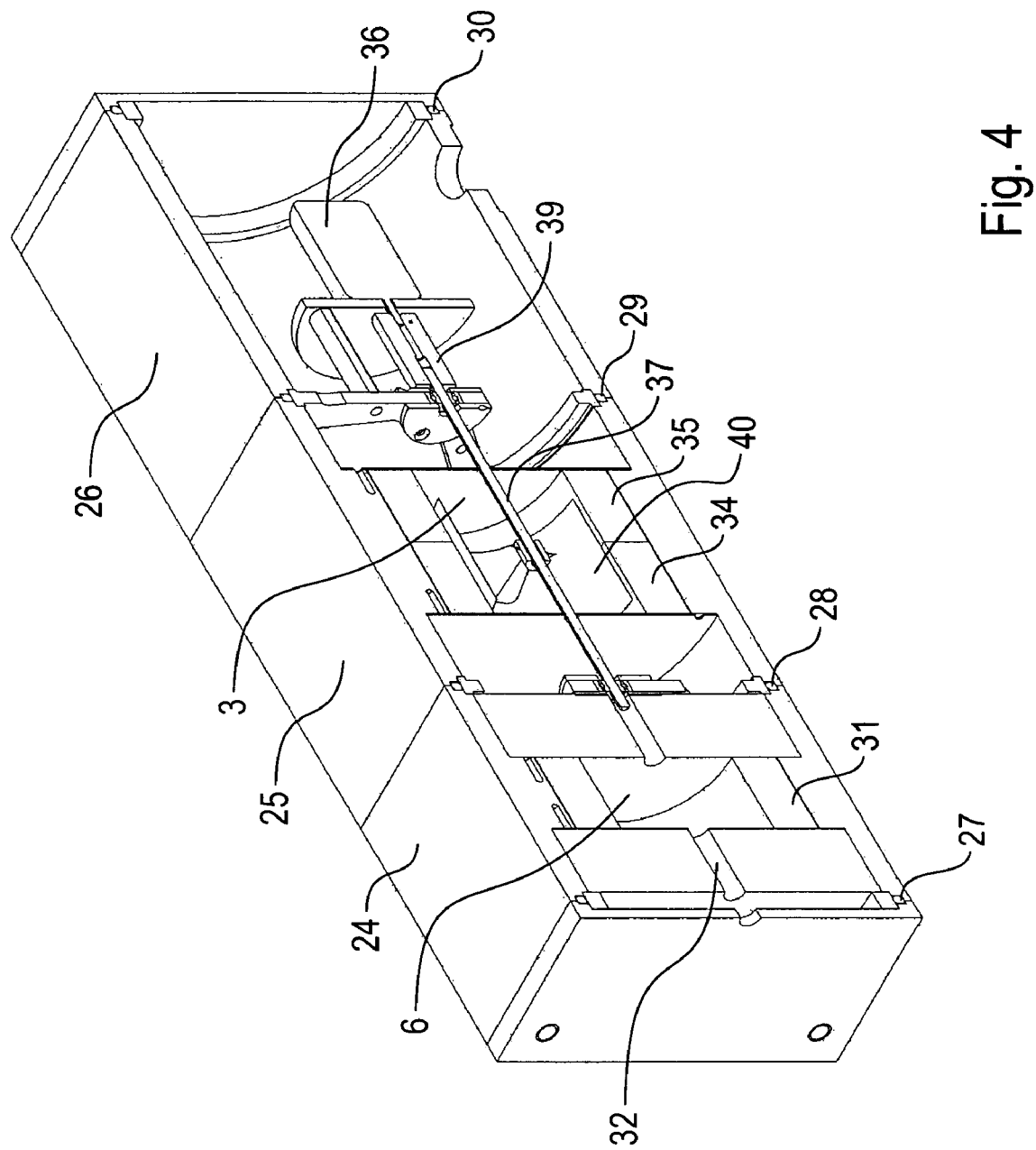

FIGS. 3 and 4 show the design of the gas chromatography apparatus described above.

The gas chromatography apparatus comprises three substantially cylindrical sections 24, 25, 26, which are gas-proof sealed by O-ring gaskets 27, 28, 29, 30.

The section 24 includes the cold trap 6, which is surrounded by a thermal insulation 31. Further, the section 24 comprises an inlet 32 for introducing the refrigerant into the cold trap 6 and an outlet 33 for pumping the refrigerant out of the cold trap 6 back to the compressor 9.

The adsorbent 5 is coil-shaped and disposed within the cylindrical cold trap 6. However, the adsorbent 5 is not shown in FIGS. 3 and 4 for the sake of clarity.

The middle section 25 of the gas chromatography apparatus includes the oven 3, which is cylindrically shaped and surrounded by thermal insulations 34, 35.

The outer section 26 includes an electric motor 36 which is connected to a rotary axis 37 of a rotary fan 38 by a coupling 39.

Further, there is a cylindrical guide plate 40 disposed within the oven 3 coaxially surrounding the rotary axis 37 of the rotary fan 38. The cylindrical guide plate 40 forms an annular gap between the cylindrical guide plate 40 and the cylindrical inner wall of the insulations 34, 35. The coiled separation column 1 is disposed within the gap although the separation column 1 is not shown in FIGS. 3 and 4 for the sake of clarity. Therefore, the rotary fan 38 generates an axially directed stream within the oven 3 which is returning to the other side via the annular gap, so that the separation column 1 disposed within the gap is effectively cooled and heated respectively.

What is claimed is:

1. A gas chromatography apparatus comprising:
    a) a cooling device, said cooling device comprising a closed cooling circuit containing a refrigerant;
    b) a heating device;
    c) an oven, said oven being heated by said heating device and being cooled by said cooling device;
    d) a separation column for separating sample components, said separation column being disposed in said oven;
    e) a cold trap being cooled by said cooling device; and
    f) an adsorbent adapted to adsorb sample components, said adsorbent being disposed in said cold trap and having a downstream connection with said separation column,
    wherein said cooling circuit comprises a first branch for cooling said oven and a second branch for cooling said cold trap, said first branch and said second branch each containing said refrigerant.

2. The gas chromatography apparatus according to claim 1, wherein said cooling device comprises:
    a) a compressor for compressing said refrigerant and for pumping said refrigerant through said cooling circuit;
    b) at least one evaporator for evaporating said compressed refrigerant thereby dissipating evaporation heat; and
    c) at least one condenser for condensing said refrigerant thereby generating evaporation heat.

3. The gas chromatography apparatus according to claim 2, wherein said evaporator is integrated in said oven.

4. The gas chromatography apparatus according to claim 1, wherein said oven is gas-proof and constitutes a part of said cooling circuit, so that said refrigerant is flowing through said oven.

5. The gas chromatography apparatus according to claim 1, wherein said cold trap and said oven are thermally insulated from each other.

6. The gas chromatography apparatus according to claim 1, wherein said cooling device is actively cooling said oven.

7. The gas chromatography apparatus according to claim 1, wherein said cooling device is actively cooling said cold trap.

8. The gas chromatography apparatus according to claim 1, further comprising a rotary fan disposed within said oven for generating a stream within said oven thereby minimizing temperature gradients within said oven.

9. The gas chromatography apparatus according to claim 8, further comprising a cylindrical guide plate disposed within said oven for guiding said stream generated by said rotary fan, said guide plate surrounding the rotary fan and being aligned substantially coaxially with said rotary fan.

10. The gas chromatograph according to claim 9, wherein said oven comprises a cylindrical inner wall, so that there is an annular gap between said guide plate and said inner wall of said oven.

11. The gas chromatography apparatus according to claim 8, wherein said oven, said cold trap and said rotary fan are aligned coaxially.

12. The gas chromatography apparatus according to claim 1, further comprising a detector for detecting different components of a sample, said separation column having a downstream connection with said detector.

13. The gas chromatography apparatus according to claim 1, wherein said separation column is a coiled pipe.

14. The gas chromatography apparatus according to claim 1, wherein said adsorbent is a coiled pipe.

15. The gas chromatography apparatus according to claim 1, wherein the gas chromatography apparatus is portable.

* * * * *